US 8,808,735 B2

(12) United States Patent
Bertelsen et al.

(10) Patent No.: US 8,808,735 B2
(45) Date of Patent: Aug. 19, 2014

(54) FAST WET-MASSING METHOD FOR THE PREPARATION OF CALCIUM-CONTAINING COMPOSITIONS

(75) Inventors: Poul Egon Bertelsen, Roskilde (DK); Peder Mohr Olsen, Kirke Hyllinge (DK); Carsten Martini Nielsen, Soborg (DK); Magnus Wilhelm Tolleshaug, Oslo (NO)

(73) Assignee: Takeda Nycomed AS, Asker (NO)

( * ) Notice: Subject to any disclaimer, the term of this patent is extended or adjusted under 35 U.S.C. 154(b) by 1577 days.

(21) Appl. No.: 11/883,536

(22) PCT Filed: Feb. 2, 2006

(86) PCT No.: PCT/IB2006/000195
§ 371 (c)(1),
(2), (4) Date: Jul. 11, 2008

(87) PCT Pub. No.: WO2006/082501
PCT Pub. Date: Aug. 10, 2006

(65) Prior Publication Data
US 2008/0317842 A1   Dec. 25, 2008

(30) Foreign Application Priority Data
Feb. 3, 2005  (DK) .................................. 2005 00168

(51) Int. Cl.
*A61K 9/48* (2006.01)
*A61K 33/10* (2006.01)
*A61K 9/20* (2006.01)

(52) U.S. Cl.
USPC ............................. 424/451; 424/464; 424/687

(58) Field of Classification Search
None
See application file for complete search history.

(56) References Cited

U.S. PATENT DOCUMENTS

| 4,830,859 A | 5/1989 | Finnan et al. |
| 4,846,409 A * | 7/1989 | Kaspar et al. ................... 241/21 |
| 5,108,728 A * | 4/1992 | Rau et al. ...................... 423/309 |

(Continued)

FOREIGN PATENT DOCUMENTS

| DE | 20216314 U1 | 12/2003 |
| EP | 0265951 | 5/1988 |

(Continued)

OTHER PUBLICATIONS

Bolhuis et al., "DC Calcium lactate, a new filler-binder for direct compaction of tablets", International Journal of Pharmaceuticals, vol. 221, 2001, pp. 77-86.

(Continued)

*Primary Examiner* — Aradhana Sasan
(74) *Attorney, Agent, or Firm* — Edwards Wildman Palmer LLP; Peter F. Corless

(57) ABSTRACT

The present invention relates to a novel process for the preparation of a granulate comprising a calcium-containing compound as an active substance. The method comprises a method for the preparation of a granulate comprising a calcium-containing compound as an active substance, the method comprising, i) feeding a granulation chamber with a composition comprising the calcium-containing compound, ii) wet-massing the composition with a granulation liquid optionally comprising a pharmaceutically acceptable binder for a time period of at the most 30 sec to obtain a wet granulate, iii) drying the thus obtained wet granulate. A granulate obtained by the present method is especially suitable in the preparation of solid dosage forms, in particular in the preparation of tablets.

28 Claims, 10 Drawing Sheets

(56) References Cited

U.S. PATENT DOCUMENTS

| | | | |
|---|---|---|---|
| 5,618,527 A | 4/1997 | Mendes et al. | |
| 5,883,047 A * | 3/1999 | Jaeger et al. | 504/367 |
| 6,149,941 A | 11/2000 | Schwarz et al. | |
| 2002/0137727 A1 | 9/2002 | Katdare et al. | |
| 2003/0021168 A1 | 1/2003 | Ishida et al. | |
| 2003/0090039 A1 | 5/2003 | Ghebre-Sellassie et al. | |
| 2003/0144306 A1 | 7/2003 | Phillips | |
| 2004/0071772 A1 | 4/2004 | Narita et al. | |
| 2005/0232989 A1 * | 10/2005 | Piene et al. | 424/464 |

FOREIGN PATENT DOCUMENTS

| | | |
|---|---|---|
| EP | 0487774 A1 | 6/1992 |
| EP | 0647591 A1 | 4/1995 |
| EP | 0872240 A1 | 10/1998 |
| EP | 0914818 A1 | 5/1999 |
| EP | 1126017 A1 | 8/2001 |
| EP | 1369131 A1 | 12/2003 |
| JP | 4235942 A | 8/1992 |
| JP | 5306229 A | 11/1993 |
| JP | 2001-316249 A | 11/2001 |
| WO | WO-92/10168 A1 | 6/1992 |
| WO | WO-95/08273 A1 | 3/1995 |
| WO | WO-96/09036 | 3/1996 |
| WO | WO-96/09036 A1 | 3/1996 |
| WO | WO-97/41835 A1 | 11/1997 |
| WO | 98/52539 A1 | 11/1998 |
| WO | WO-99/06051 A1 | 2/1999 |
| WO | WO-99/61037 | 12/1999 |
| WO | WO-00/24274 | 5/2000 |
| WO | WO-00/28973 | 5/2000 |
| WO | 00/76650 A1 | 12/2000 |
| WO | 01/83374 A2 | 11/2001 |
| WO | WO-03/055500 A1 | 7/2003 |

OTHER PUBLICATIONS

Bruynseels, et al., "Fluidized-bed process fully established and still developing", Nitrogen No. 183, Jan.-Feb. 1990, pp. 22-26.

CPhI Celebrates ten years of growth in Frankfurt—Manufacturing Chemist, Dec. 31, 1999.

"Excipient Systems", http://www.merck.de/english/services/specialchemie/s_chn/pharma/excipients.htm, Jul. 11, 2000.

Merck Formaxx products—marketing information, Sep. 16, 2004.

Oneda et al., "The effect of formulation variables on the dissolution and physical properties of spray-dried microspheres containing organic salta", Power Technology, vol. 130, 2003, pp. 377-384.

Rumpler et al., "Continuous Agglomeration and Granulation by Fluidization", Food Marketing & Technology, Apr. 1999, pp. 1-3.

"2.9.8. Resistance to Crushing of Tablets" European Pharmacopoeia 7.0 p. 267 Jan. 2008:20908.

"2.9.3. Dissolution Test for Solid Dosage Forms" European Pharmacopoeia 7.0 pp. 256-263 Jan. 2010:20903 corrected 6.8.

"2.9.7. Friability of Uncoated Tablets" European Pharmacopoeia 7.0 p. 266 Jan. 2010:20907.

"2.9.1. Disintegration of Tablets and Capsules" European Pharmacopoeia 7.1 pp. 3331-3332 Apr. 2011:20901.

Klobes P et al. "Porosity and Specific Surface Area Measurements for Solid Materials" NIST, (SP 960-17), Sep. 2006.

* cited by examiner

PCA analysis based on experiments 1 – 5, 8 – 12 and 14 + 15.

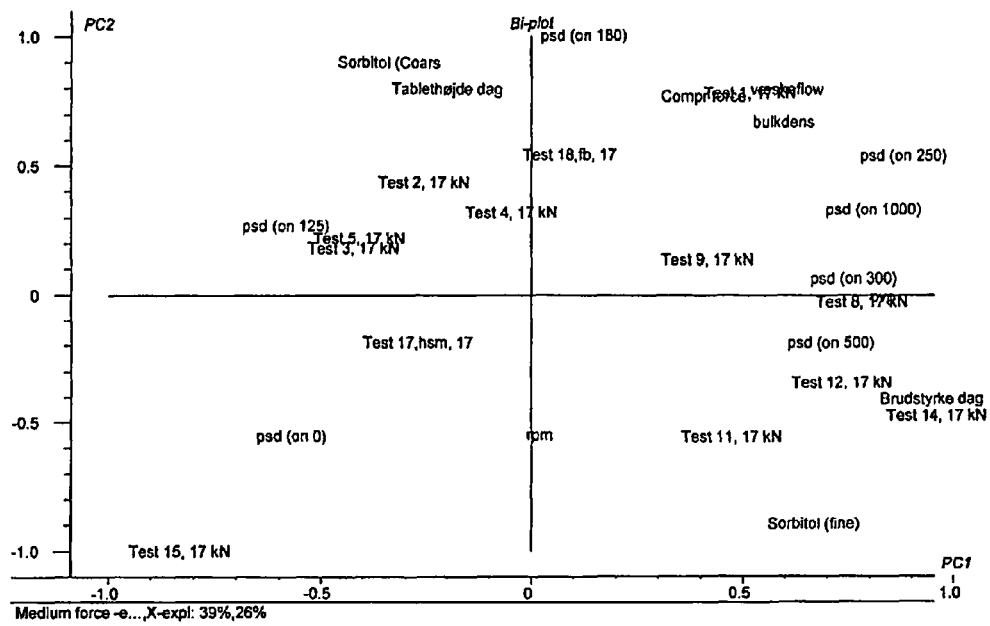

Explanation of legends:
Tablethøjde dag = Tablet height
Væskeflow = Liquid flow rate
psd (on 0) = amount of granulate on sieve 0 which equals amount of granulate in the interval between 0 to 125 μm
Brudsty = Tablet crushing strength
Test 1 to 9 corresponds to exp. 1 to 9
Test 11 corresponds to exp. 10
Test 12 corresponds to exp. 11
Test 14 corresponds to exp. 12
Test 17 corresponds to exp. 14
Test 18 corresponds to exp. 15

Fig. 1

PCA analysis based on experiments 1 – 5, 8 – 13 and 14 + 15 including an estimate of amount of granulate on sieve 150 µm.

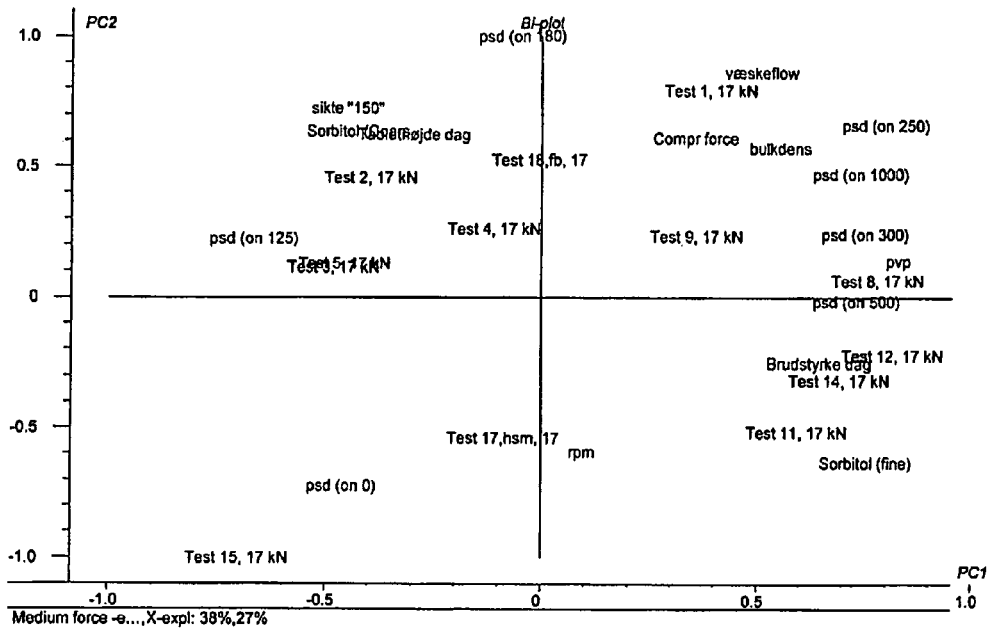

Explanation of legends:
Tablethøjde dag = Tablet height
Væskeflow = Liquid flow rate
psd (on 0) = amount of granulate on sieve 0 which equals amount of granulate in the interval between 0 to 125 µm
Brudsty = Tablet crushing strength
Test 1 to 9 corresponds to exp. 1 to 9
Test 11 corresponds to exp. 10
Test 12 corresponds to exp. 11
Test 14 corresponds to exp. 12
Test 17 corresponds to exp. 14
Test 18 corresponds to exp. 15

Fig. 2A

FAST WET-MASSING METHOD FOR THE PREPARATION OF CALCIUM-CONTAINING COMPOSITIONS

FIELD OF THE INVENTION

The present invention relates to a novel process for the preparation of a granulate comprising a calcium-containing compound as an active substance. A granulate obtained by the present method is especially suitable in the preparation of solid dosage forms, in particular in the preparation of tablets.

BACKGROUND OF THE INVENTION

Calcium is essential for a number of key functions in the body, both as ionized calcium and a calcium complex. A number of diseases, especially bone-related diseases, are treated/prophylactically treated by intake of a sufficient amount of a calcium-containing compound. Normally, calcium must be orally administered in a relatively high amount, which makes especially dosage forms like e.g. chewable or suckable tablets suitable. However, one of the major problems in this respect is to obtain compositions that have a sufficient customer compliance in order to achieve a correct and efficient treatment. This problem is related to the unpleasant taste and/or mouth feel of calcium-containing compounds, which taste and/or mouth feel is very difficult to mask. Accordingly, the development regarding calcium-containing products for pharmaceutical or nutriceutical use is mainly focused on this taste-masking aspect. To this end, a number of different ways of achieving a suitable taste-masking of a calcium-containing compound have emerged including different manufacturing processes, use of various taste-masking agents and combinations thereof etc.

Another major problem in relation to formulation of calcium-containing solid dosage forms is the size of the dosage form. Normally, a single dose of calcium equals 500 mg (12.5 mmol), which means that, when calcium carbonate is used as calcium source, a single dose contains 1250 mg of calcium carbonate (MW of calcium carbonate is 100). Furthermore, addition of pharmaceutically acceptable excipients is normally required in order to enable tabletting of the calcium-containing compound. This means that the resulting tablet containing a single dose of calcium has a relatively high weight and accordingly, the volume of the tablet is relatively high. It is therefore of utmost importance to seek to minimize the size of the dosage form (e.g. normally in the form of a tablet) as much as possible so that the patient does not find it unpleasant to take the tablet. The size of the tablets is of course of most importance in case of tablets intended for oral administration (to be swallowed). Alternatively, the size of chewing tablets is not that important provided that tablets containing a relevant single dose can be manufactured by means of conventional tabletting equipment. However, in the case dose dispensing is needed the size is critical. Furthermore, chewing tablets should not be too hard to chew, i.e. they should have a crushing strength, which balances the easiness of chewing the tablet and the importance of robustness in order to withstand the normal handling of the tablets. Furthermore, the mouth feel and the taste are of utmost importance in order to ensure patient compliance.

It has been found that the particular method for preparing a particulate material containing the calcium-containing compound influences the taste and mouth-feel of the final product. Thus, it has been found that e.g. a fluid-bed method enables preparation of calcium-containing particulate material that when compressed into tablets have an acceptable taste and mouth-feel in use. In this case, the quality of the calcium-containing compound as well as the method for preparation of a pharmaceutical composition containing the calcium-containing compound are of great importance in order to obtain acceptable taste and mouth feel of a chewable tablet (WO 00/28973). The granulates obtained by this process are manufactured into tablets that have suitable sensory properties, i.e. acceptable mouth feel and taste. However, such tablets must have a suitable small size, a suitable mechanical stability and a suitable mechanical strength to withstand exposure to filling e.g. via a dose-dispensing machine. Furthermore, a fluid-bed process often lead to a very porous granulate which in turn lead to porous tablets, i.e. such tablets may be too large to fit into the cassettes of dose-dispensing machines.

Moreover, the fluid-bed method is not generally applicable to e.g. tablets intended to be sucked or swallowed. The reason is that calcium is dosed in a relatively high amount and in order to include this dosage in a single dosis form (tablet), the size of the tablet becomes inconveniently large for a patient to swallow. Accordingly, the fluid-bed process is particular useful in the preparation of chewable tablets.

Calcium-containing tablets suitable for swallowing (i.e. prepared without taking the chalky taste and mouth-.feel of the calcium-containing compound into consideration) can be prepared by a process involving e.g. high-shear mixing (WO 96/09036 to Innothera). By using this process a relatively dense granulate is obtained, which in turn leads to tablets of a size that is reduced compared to that obtained when a fluid-bed process is used.

The problem addressed by the present inventors is to provide an alternative method that without preference enables the preparation of a dosage form of a calcium-containing compound in the form of chewable tablets as well as in the form of swallowable tablets. In other words, the known processes are either suitable for use in the preparation of chewable tablets or in the preparation of swallowable tablets. In contrast thereto, a method according to the invention can be used both to prepare chewable tablets and swallowable tablets, respectively.

Such a process has high economical potential, as it will be possible to use the same apparatus in the production of tablets irrespective of whether they are intended for chewing or swallowing. Accordingly, the same production line can easily be shifted from one process to the other and it is not necessary to invest in two separate and different production equipment.

Accordingly, there is a need for developing novel methods that enable preparation of dosage forms like tablets that have a reduced and convenient size for a patient to swallow it and, moreover, also can be used in the preparation of chewable tablets.

BRIEF DESCRIPTION OF THE DRAWINGS

FIG. 1 illustrates the principal component analysis (PCA) based on experiments 1-5, 8-12 and 14+15.

FIG. 2A illustrates the PCA based on experiments 1-5, 8-13 and 14+15 including an estimate of amount of granulate on sieve 150 µm.

DESCRIPTION OF THE INVENTION

Figures 2B, 2C:
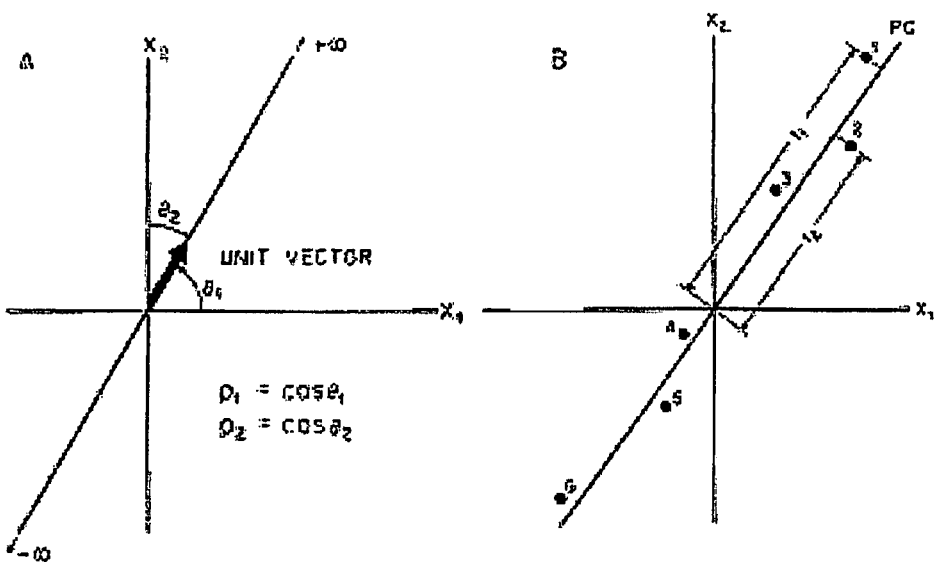
FIG. 2B describes how to compare principle components in a bi-plot.
FIG. 2C describes how to compare principle components in a bi-plot.
Figure 3:
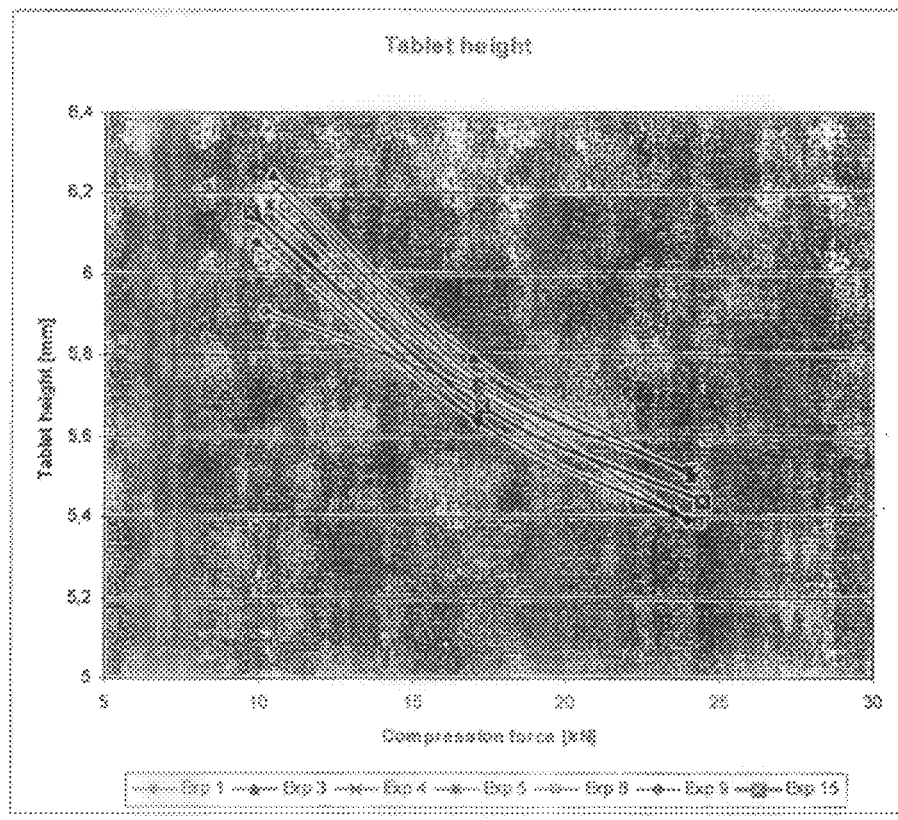
FIG. 3 illustrates the tablet height from experiments 1, 3, 4, 5, 8 and 9 compared with fluid bed (experiment 15).
Figure 4:
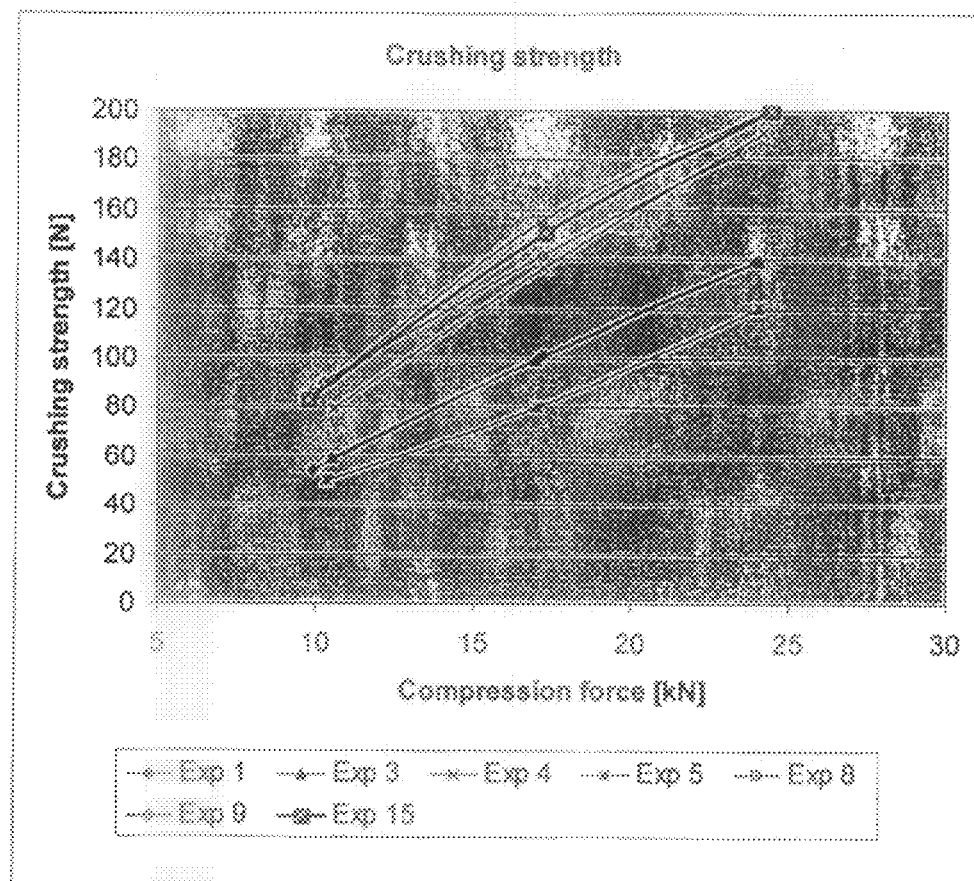
FIG. 4 illustrates the tablet crushing strength from experiments 1, 3, 4, 5, 8 and 9 compared with fluid bed (experiment 15).
Figure 5:
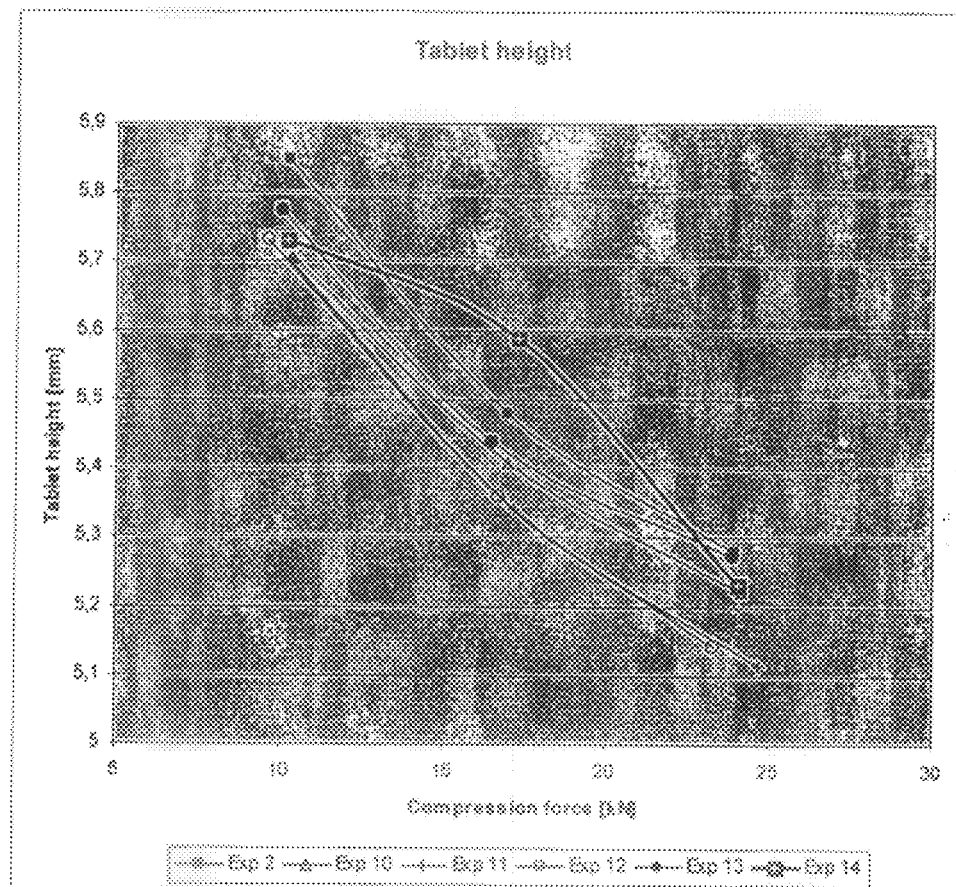
FIG. 5 illustrates the tablet height from experiments 2, 10, 11, 12 and 13 compared with high shear mixer (experiment 14).
Figure 6:
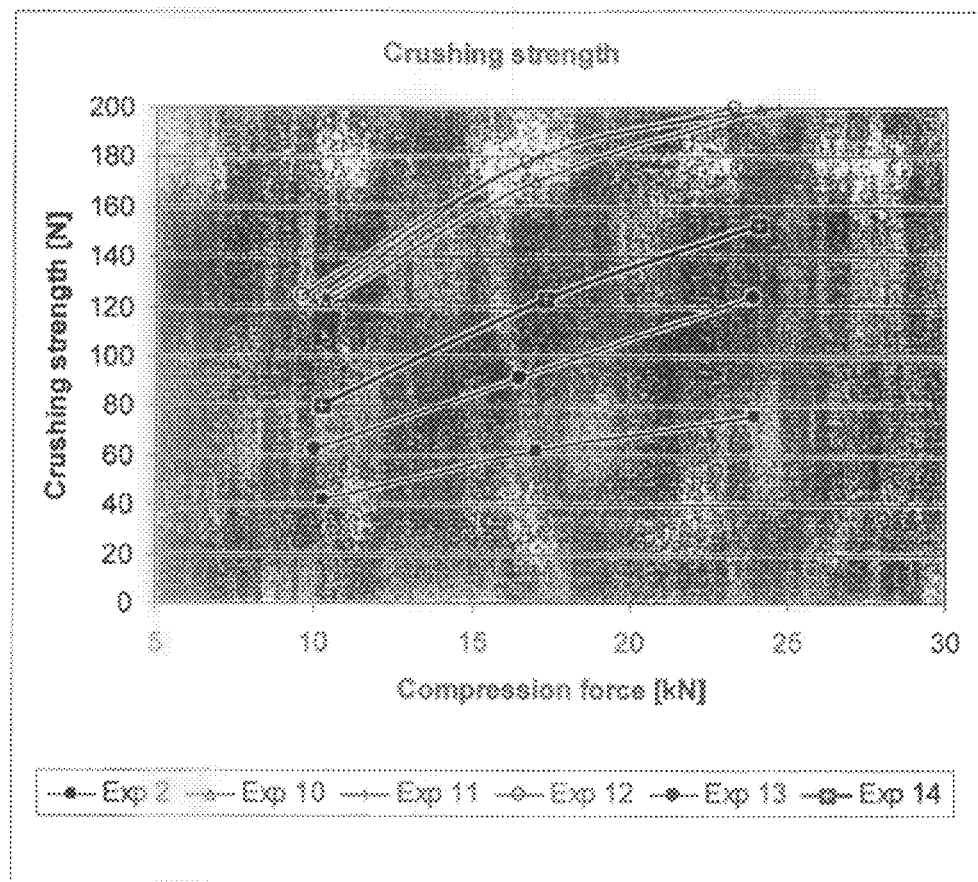
FIG. 6 illustrates the tablet crushing strength from experiments 2, 10, 11, 12 and 13 compared with high shear mixer (experiment 14).

The present invention thus provides a method for the preparation of a granulate comprising a calcium-containing compound as an active substance, the granulate being suitable for preparing a dosage form in the form of chewable tablets as well as in the form of swallowable tablets, the method comprising, i) feeding a granulation chamber with a composition comprising the calcium-containing compound, ii) wet-massing the composition with a granulation liquid comprising a pharmaceutically acceptable binder for a time period of at the most 30 sec to obtain a wet granulate, iii) drying the thus obtained wet granulate.

It has been found that a very short and intensive step of application of the granulation liquid and wet-massing of the composition comprising the calcium-containing compound leads to a granulate that is suitable for the preparation of chewable, suckable or swallowable tablets. Especially with regard to chewable tablets it is believed that the very short processing time of the step mentioned above allows similar or higher porosity (compared with known processes like fluid-bed and high-shear mixing), which in turn leads to a much better wettability of the tablet upon exposure to saliva in the oral cavity. The much better wettability of the tablet leads to a sensing of an improved taste (i.e. the chalky feeling and taste of calcium is less pronounced) and mouth-feel.

The process time for the step of application, of the granulation liquid and wet-massing may vary depending on the equipment employed. In a specific embodiment, the wet-massing in step ii) is carried out in a time period of at the most about 20 sec such as, e.g., at the most about 15 sec, at the most about 10 sec or at the most about 5 sec.

An especially suitable apparatus for use in the present method is manufactured by Hosokawa Micron. The model Schugi Flexomix FX-160 has been employed in the examples herein, but the invention is not limited to the use of this particular model, other models and apparatus having a similar construction leading to a very fast step of wet-massing as mentioned above, are also within the scope of the present invention. In e.g. the Schugi Flexomix, the wet-massing in step ii) is carried out in a time period of at the most about 1 sec preferably at the most about 0.5 sec, at the most about 0.4 sec, at the most about 0.3 sec or at the most about 0.2 sec Depending on the size of the apparatus employed, the feeding rate of the granulation chamber with the calcium-containing composition as well as the flow rate of the granulation liquid may vary.

Normally, in apparatus as that used in the examples herein the granulation chamber is feeded with a feeding rate of from about 200 to about 1000 kg/h such as, e.g., from 300 to about 850 kg/h, from about 300 to about 750 kg/h, from 300 to about 700 kg/h, from about 350 to about 650 kg/h, from about 400 to about 600 kg/h, from about 450 to about 550 kg/h such as about 500 kg/h.

In equipments intended for very fast production, the granulation chamber is feeded with a feeding rate of from about 1000 to about 1500 kg/h such as, e.g., about 1100 to about 1300 kg/h.

The liquid flow of the granulation liquid is also an important parameter in order to obtain a fast and efficient step of application of the granulation liquid and wet-massing the composition. Normally, the granulation liquid is sprayed on the composition at a spray rate in a range of from about 15 to about 100 kg/h. Again, the flow rate depends on the size of the equipment, a larger equipment enables a higher flow rate than a smaller equipment. Furthermore, the choice of flow rate is an important parameter for preparing chewable and swallowable tablets, respectively. From the examples herein a person skilled in the art can find guidance as to how to select the right flow rate depending on the desired dosage form. In the apparatus employed in the examples, the granulation liquid is sprayed on the composition at a spray rate in a range of from about 15 to about 80 kg/h such as, e.g., from about 20 to about 60 kg/h, from about 20 to about 50 kg/h, from about 20 to about 40 kg/h or from about 25 to about 35 kg/h. A person skilled in the art will know how to adjust the liquid flow depending on the equipment employed. As a guidance for larger equipment than that employed in the examples, the granulation liquid may be sprayed on the composition at a spray rate in a range of from about 50 to about 300 kg/h such as, e.g., from about 60 to about 200 kg/h from about 65 to about 150 kg/h, from about 70 to about 125 kg/h or from about 75 to about 105 kg/h.

The continuous feeding of the powder composition as well as of the granulation liquid enables the process to be continuous, i.e. it may be continuously for a period of 1 day or more such as, e.g., 2 days or more, a 3 days or more, 4 days or more, 5 days or more or 7 days or more. In principle, the time period is determined based on the amount of granulate to be produced, but it may eventually be interrupted by clogging of parts of the apparatus that need to be rinsed.

In a specific embodiment using the Schugi Flexomix equipment (or a similar apparatus) the composition comprising the calcium-containing compound is fed through the top of the granulation chamber and passes through the chamber by means of gravity. The chamber contains a number of knives that enable an intensive wet-massing of the composition. Compared with a high-shear mixing process the step of application of the granulation liquid and the wet-massing according to the present method is much faster.

The composition comprising the calcium-containing compound may consist of the calcium-containing compound as such or it may also comprise one or more pharmaceutically acceptable excipients such as described herein. If it is desired to prepare a combination product, i.e. a product containing more than one therapeutically, prophylactically and/or diagnostically active substance, the composition may also comprise one or more of such substances. To this end it should be mentioned that combination products of calcium and a nutrient like e.g. vitamin D already are on the market and have proved to be efficient in therapy. However, due to vitamin D sensibility towards humidity and oxidation, vitamin D is normally added to the granulate before e.g. compressing the granulate into tablets, i.e. vitamin D is not subjected to the granulation step of the process according to the invention.

Calcium-Containing Compound

The calcium-containing compound contained in a granulate made according to the invention is a physiologically tolerable calcium-containing compound that is therapeutically and/or prophylactically active.

As mentioned above, calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779:201-16). The secretion of hormones and the activity of key enzymes and proteins are dependent on calcium. Finally calcium as a calcium phosphate complex confers rigidity and strength on the skeleton (Boskey A L. Springer, 1988:171-26). Because bone contains over 99% of the total body calcium, skeletal calcium also serves as the major long-term calcium reservoir.

Calcium salts such as, e.g., calcium carbonate or calcium phosphate is used as a source of calcium especially for patients suffering from or at risk of osteoporosis. Moreover, calcium carbonate is used as an acid-neutralizing agent in antacid tablets.

As mentioned above, calcium has a number of important functions within the mammalian body in particular in humans. Furthermore, in many animal models, chronic low calcium intake produces osteopenia. The osteopenia affects cancellous bone more than cortical bone and may not be completely reversible with calcium supplementation. If the animal is growing reduced calcium intake leads to stunting. In the premature human neonate the higher the calcium intake, the greater the increase in skeletal calcium accretion which, if high enough, can equal gestational calcium retention. During growth chronic calcium deficiency causes rickets. Calcium supplements in both pre- and postpubertal healthy children leads to increased bone mass. In adolescents the higher the calcium intake, the greater the calcium retention, with the highest retention occurring just after menarche. Taken together, these data suggest that in children and adolescents considered to be taking an adequate intake of calcium, peak bone mass can be optimized by supplementing the diet with calcium. The mechanisms involved in optimizing deposition of calcium in the skeleton during growth are unknown. They are probably innate properties of the mineralization process that ensures optimal calcification of the osteoid if calcium supplies are high. The factors responsible for stunting of growth in states of calcium deficiency are also unknown but clearly involve growth factors regulating skeletal size.

In adults calcium supplementation reduces the rate of age-related bone loss (Dawson-Hughes B. Am J Clin Nut 1991; 54:S274-80). Calcium supplements are important for individuals who cannot or will nor achieve optimal calcium intakes from food. Furthermore, calcium supplement is important in the prevention and treatment of osteoporosis etc.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 466 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablets did. Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

A calcium-containing compound for use according to the invention may be e.g. bisglycino calcium, calcium acetate, calcium carbonate, calcium chloride, calcium citrate, calcium citrate malate, calcium comate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Other calcium sources may be water-soluble calcium salts, or complexes like e.g. calcium alginate, calcium-EDTA and the like or organic compounds containing calcium like e.g. calcium organophosphates. Use of bone meal, dolomite and other unrefined calcium sources is discouraged because these sources may contain lead and other toxic contaminants. However, such sources may be relevant if they are purified to a desired degree.

The calcium-containing compound may be used alone or in combination with other calcium-containing compounds.

Of specific interest is bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Mixtures of different calcium-containing compounds may also be used. As appears from the examples herein, calcium carbonate and calcium phosphates are especially suitable for use as a calcium-containing compound and calcium carbonate, tricalcium phosphate ($Ca_5(PO_4)OH$) and β-tricalcium phosphate ($Ca_3(PO_4)$) have a high content of calcium, whereas dicalcium phosphate ($CaHPO_4$) has a lower content of calcium but is available in high density qualities.

Of particular interest is calcium carbonate and calcium phosphate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium Carbonate

Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite 1A+B from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL.

Calcium carbonate 2064 Merck (available from Merck, Darmstadt, Germany) that has a mean particle size of 10-30 μm, an apparent bulk density of 0.4 to 0.7 g/mL, and a specific surface area of 0.3 $m^{21}$ g;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant SA, France) has a mean particle size of 5 to 20 μm, an apparent bulk density of 0.7 to 1.0 g/mL, and a specific surface area of 0.6 $m^2$/g;

Scoralite 1B (available from Scora Watrigant SA, France) has a mean particle size of 10-25 μm, an apparent bulk density of 0.9 to 1.2 g/mL, and a specific surface area of 0.4 to 0.6 $m^2$/g;

Scoralite 1A+B (available from Scora Watrigant SA, France) have a mean particle size of 7-25 μm, an apparent bulk density of 0.7 to 1.2 g/mL, and a specific surface area of 0.35 to 0.8 $m^2$/g;

Pharmacarb LL (available from Chr. Hansen, Mahawah New Jersie) L has a mean particle size of 12-16 μm, an apparent bulk density of 1.0 to 1.5 g/mL, and a specific surface area of 0.7 $m^2$/g;

Sturcal H (available from Specialty Minerals, Bethlehem, Pa.) has a mean particle size of approx. 4 μm, an apparent bulk density of 0.48 to 0.61 g/mL;

Sturcal F (available from Specialty Minerals, Bethlehem, Pa.) has a mean particle size of approx. 2.5 μm, an apparent bulk density of 0.32 to 0.43 g/mL;

Sturcal M (available from Specialty Minerals, Bethlehem, Pa.) has a mean particle size of 7 μm, an apparent bulk density of 0.7 to 1.0 g/mL, and a specific surface area of 1.5 $m^2$/g;

Sturcal L (available from Specialty Minerals, Bethlehem, Pa.) has a mean particle size of approx. 7 μm, an apparent bulk density of 0.78 to 0.96 g/mL, Sturcal L consists of scalenohedral shaped crystals;

Socal P2PHV (available from Solvay, Brussels, Belgium) has a mean particle size of 1.5 μm, an apparent bulk density of 0.28 g/mL, and a specific surface area of 7.0 $m^2$/g Socal P2PHV consists of scalenohedral shaped crystals;

Mikhart 10, SPL, 15, 40 and 65 (available from Provencale, Provencale, France);

Mikhart 10 has a mean particle size of 10 μm,

Mikhart SPL has a mean particle size of 20 μm,

Mikhart 15 has a mean particle size of 17 μm,

Mikhart 40 has a mean particle size of 30 μm, an apparent bulk density of 1.1 to 1.5 g/mL;

Mikhart 65 has a mean particle size of 60 μm, an apparent bulk density of 1.25 to 1.7 g/mL;

Hubercal Elite 500 (available from J. M. Huber Corp., USA) has a mean particle size of 5.8 μm and a specific surface area of 1.8 $m^2$/g;

Hubercal Elite 500 (available from J. M. Huber Corp., USA) has a mean particle size of 8.2 μm and a specific surface area of 1.3 $m^2$/g.

Omyapure 35, (available from Omya S. A. S, Paris, France) has a mean particle size of 5-30 μm, and a specific surface area of 2.9 $m^2$/g;

Calci Pure 250 Heavy, Calci Pure 250 Extra Heavy and Calci Pure GCC HD 212 with a mean particle size of 10-30 μm, an apparent bulk density of 0.9-1.2 g/ml, and a specific surface area of 0.7 $m^{21}$ g (available from Particle Dynamic Inc., St. Louis Montana).

Calcium Phosphate

DI-CAFOS A ($CaHPO_4$) (available from Chemische Fabrik Buddenheim KG, Buddenheim, Germany) that has a mean particle size of approximately 70 μm and a bulk density of approximately 1.3 g/ml and a polycrystallic and porous nature;

DI-CAFOS PA ($CaHPO_4$) (available from Chemische Fabrik Buddenheim KG, Buddenheim, Germany) that has a mean particle size <7 μm and a bulk density of approximately 0.9 g/ml;

TRI-CAFOS P($Ca_5(PO_4)_3OH$ (available from Chemische Fabrik Buddenheim KG, Buddenheim, Germany) that has a mean particle size <6 μm and a bulk density of approximately 0.25 g/ml and a polycrystalic and porous nature;

TRI-CAFOS S ($Ca_5(PO_4)_3OH$) (available from Chemische Fabrik Buddenheim KG, Buddenheim, Germany) that has a mean particle size of approximately 70 μm and a bulk density of approximately 0.5 g/ml;

CAFOS DB ($Ca_3(PO_4)_2$ (available from Chemische Fabrik Buddenheim KG, Buddenheim, Germany) that has a mean particle size <5 μm and a bulk density of approximately 0.6 g/ml;

Other qualities may also be suitable for use according to the invention.

The content of the calcium-containing compound in a tablet made according to the present invention is in a range from about 40% to about 100% w/w such as, e.g., from about 45% to about 98% w/w, from about 50% to about 95% w/w, from about 55% to about 90% wow or at least about 60% w/w, at least about 65% w/w, at least about 70% w/w or at least about 75% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted to that the tablets are suitable for administration 1-4 times daily, preferably once or twice daily.

Granulation Liquid

In order to obtain agglomeration of the composition containing the calcium-containing compound a binder, especially a water-soluble binder is useful. The binder may be added to the composition containing the calcium-containing compound or it may be added in the form of a granulation liquid. In a specific embodiment, the binder is included in the composition containing the calcium-containing compound. The granulation liquid is normally based on water although organic solvents like e.g. alcohol (e.g. ethanol, isopropanol) may be added.

In a specific embodiment the binder is selected from water-soluble binders.

Examples of suitable binders include e.g. dextrins, maltodextrins (e.g. Lodex® 5 and Lodex® 10), dextrose, fructose, glucose, inositol, erythritol, isomalt, lactitol, lactose (e.g., spray-dried lactose, α-lactose, β-lactose, Tabletose®, various grades of Pharma-tose®, Microtose or Fast-Floc®), maltitol, maltose, mannitol, sorbitol, sucrose, tagatose, trehalose, xylitol, low-substituted hydroxypropylcellulose (e.g. LH 11, LH 20, LH 21, LH 22, LH 30, LH 31, LH 32 available from Shin-Etsu Chemical Co.), microcrystalline cellulose (e.g., various grades of Avicel®, such as Avicel® PH101, Avicel® PH102 or Avicel® PH105, Elcema® P100, Emcocel®, Vivacel®, Ming Tais and Solka-Floc®), starches or modified starches (e.g. potato starch, maize starch, rice starch, pregelatinised starch), polyvinylpyrrolidone, polyvinylpyrrolidonelvinyl acetate copolymer, agar (e.g. sodium alginate), carboxyalkylcellulose, dextrates, gelatine, gummi arabicum, hydroxypropyl cellulose, hydroxypropylmethylcellulose, methylcellulose, polyethylene glycol, polyethylene oxide, polysaccharides e.g. dextran, soy polysaccharide.

In an embodiment of particular interest involving wet granulation, the binder is PVP 30, PVP 90 or mixtures thereof. In general, the concentration is from about 0.1 to about 10% w/w such as, e.g., from about 0.2 to about 8% w/w, from about 0.3 to about 7% w/w, from about 0.4 to about 6% w/w or from about 0.4 to about 5% w/w.

Another type of binder may be a sugar alcohol such as those mentioned herein. Thus, in interesting embodiments it is convenient to use a sugar alcohol that has properties like a binder, i.e. to a certain extent it is capable of establishing binding between the individual particles in the composition and further in the binding during compression into coherent tablets. Thus, such sugar alcohols with binding properties facilitate the agglomeration process as well as the tabletting process.

Figure 9:
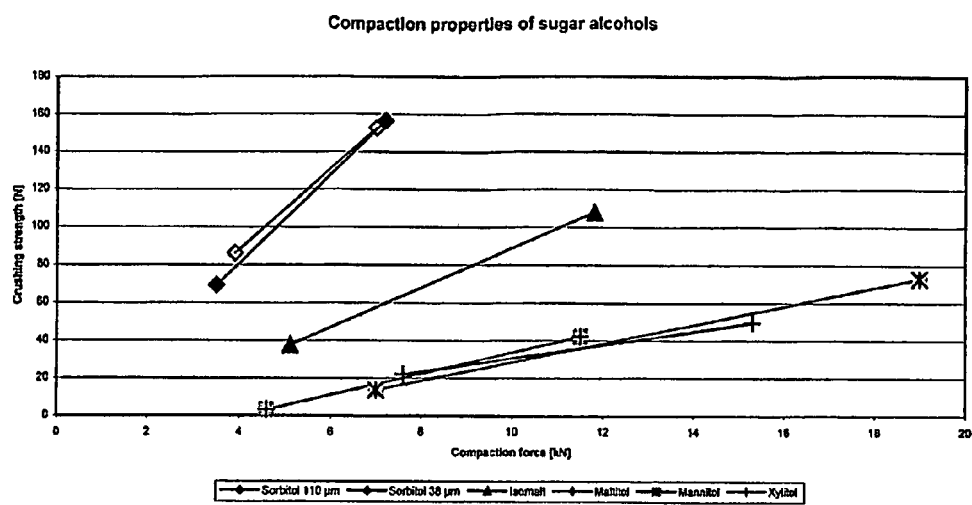
FIG. 9 illustrates the compaction properties of sugar alcohols.

A sugar alcohol suitable for use in methods according to the invention is selected from the group consisting of isomalt, mannitol, sorbitol, xylitol, inositol, erythritol, lactitol, maltitol, and the like, and mixtures thereof. Normally, the concentration of the sugar alcohol in the composition comprising the calcium-containing compound is from about 5% to about 40% w/w such as, e.g., from about 5% to about 35% w/w, from about 10% to about 30% w/w, from about 10% to about 30% w/w, from about 10% to about 25% w/w. In general all the mentioned sugar alcohols may be used as binders. However, the amounts required to obtain suitable binding are dependent on the binding properties of the sugar alcohol in question. FIG. 9 herein gives a graphical representation of crushing strength as a function of compaction force for various sugar alcohols and from this graph it is seen that sugar alcohols with lower slopes are required in higher amounts than sugar alcohols with steeper slopes.

The concentration of the binder in the composition comprising the calcium-containing compound may vary over a great range depending on the particular binder employed, but in general it is between from about 0.1% to about 40% w/w such as, e.g. from about 0.2 to about 35% w/w, from about 0.3 to about 30% w/w or from about 0.4 to about 25% w/w or from about 0.4 to about 24.2% w/w. In particular, if PVP is employed as a binder, the concentration is normally in the lower range such as from about 0.1 to about 1% w/w, whereas in the case of sorbitol, the concentration is normally about 20-30% w/w and in the case of sugar alcohols other than sorbitol, the concentration is normally in the higher range such as from about 30 to about 40% w/w.

Irrespective of whether a sugar alcohol has been employed as a binder or not, one or more sugar alcohols (e.g. such as those mentioned hereinbefore) are included in specific embodiments. The sugar alcohols have sweetening and taste masking properties in themselves, which make them especially suitable for use in the present context. The concentration of the sugar alcohol in the composition comprising the calcium-containing compound (or, alternatively, in the granulate obtained) is from about 5% to about 40% w/w such as, e.g., from about 5% to about 35% w/w, from about 10% to about 30% w/w, from about 10% to about 30% w/w, from about 10% to about 25% w/w. However, in the case that the sugar alcohol or a mixture of sugar alcohols are employed as the sole binder(s), the total concentration of sugar alcohol is normally at least 10% w/w such as e.g. at least 15% wow or at least 20% w/w. Normally, the concentration does not exceed 40% w/w.

Preferably, the granulation liquid is an aqueous medium. In the case where the binder is included in the granulation liquid, the granulation liquid is prepared by dissolving the binder in water. Alternatively the binder can be admixed in a dry form to the powder.

The wet granulate is subjected to drying in a suitable drying chamber. It may be a drying chamber that is coupled to the granulation apparatus e.g. a vertical or horizontal positioned fluid bed both batch wise or continuous.

As mentioned above, the granulate obtained by the method according to the invention may be used as such, but it is also very suitable for further manufacturing into solid dosage forms like e.g. tablets, capsules or sachets.

In the examples herein guidance is given of which parameters that are important to take into account and how to select a suitable set-up in order to prepare chewable tablets or swallowable tablets, respectively. Based on this guidance a person skilled in the art will know how to adjust the composition and the various process parameters in order to obtain a desired calcium-containing product.

In one embodiment of the invention, the granulate obtained by the present method is intended to be manufactured into tablets. Often it is necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., $D_3$ vitamin, $D_2$ vitamin or derivatives thereof.

D Vitamin or Other Active Substances

A granulate or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K and minerals like e.g. zinc, magnesium, selenium etc.

Of particular interest are one or more D-vitamin compounds such as, e.g., Vitamin $D_2$ (ergocalciferol) and Vitamin $D_3$ (cholecalciferol) including dry vitamin $D_3$, 100 CWS available from Roche and dry vitamin $D_3$ 100 GFP available from BASF.

In addition to its action on calcium and skeletal homeostasis, vitamin D is involved in the regulation of several major systems in the body. The actions of vitamin D are medicated at the genome by a complex formed by 1,25(OH)$_2$ vitamin D mainly produced in the kidney, with the vitamin D receptor (VDR). The latter is widely distributed in many cell types. The 1,25-(OH)$_2$ vitamin DNDR complex has important regulatory roles in cell differentiation and in the immune system. Some of these actions are probably dependant on the ability of certain tissues other than the kidney to produce 1,25-(OH)$_2$ vitamin D locally and act as a paracrine (Adams J S et al. Endocrinology 1996; 137:4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993:83-118). It is not clear whether this delay is due to a failure of a 1,25-(OH)$_2$ vitamin D-dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcaemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-$(OH)_2$ vitamin D due to a reduction in its substrate 25-OHD (Francis R M et al. Eur J Clin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-$(OH)_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent findings suggest trends of need for higher doses of vitamin D for the elderly patients (Compston J E. BMJ 1998; 317:1466-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Heikinheimo R J et al. Calcif Tissue Int 1992; 51:105-110).

As it appears from above, a combination of calcium and vitamin D is of interest. The recommended Daily Allowance (RDA) of calcium and vitamin $D_3$ are as follows (European Commission. Report on osteoporosis in the European Community. Action for prevention. Office for official Publications of the European Communities, Luxembourg 1998):

| Group | Age (years) | Calcium (mg)* | Vitamin $D_3$ (µg) |
|---|---|---|---|
| Newborn | 0-0.5 | 400 | 10-25 |
|  | 0.5-1.0 | 360-400 | 10-25 |
| Children | 1.0-3.0 | 400-600 | 10 |
|  | 4.0-7.0 | 450-600 | 0-10 |
|  | 8.0-10 | 550-700 | 0-10 |
| Men | 11-17 | 900-1000 | 0-10 |
|  | 18-24 | 900-1000 | 0-15 |
|  | 25-65 | 700-800 | 0-10 |
|  | 65+ | 700-800 | 10 |
| Women | 11-17 | 900-1000 | 0-15 |
|  | 18-24 | 900-1000 | 0-10 |
|  | 25-50 | 700-800 | 0-10 |
|  | 51-65 | 800 | 0-10 |
|  | 65+ | 700-800 | 10 |
| Pregnant |  | 700-900 | 10 |
| Lactating |  | 1200 | 10 |

*RDA of calcium varies from country to country and is being re-evaluated in many countries.

Vitamin D is very sensitive towards humidity and is subject to degradation. Therefore, vitamin D is often administered in a protective matrix. Accordingly, when tablets are prepared containing a vitamin D it is of utmost importance that the compression forces applied during the tabletting step do not decrease the protective effect of the matrix and thereby impair the stability of vitamin D. To this end, the combination of the various ingredients in a granulate or tablet made according to the invention has proved to be very suitable in those cases where vitamin D also is incorporated into the composition as it is possible to employ a relatively low compression force during tabletting and still achieve a tablet with suitable mechanical strength (crushing strength, friability etc.).

Accordingly, the compression step is performed at a compression force that is adjusted with respect to the diameter and the desired height of the tablet so that the compression force applied is at the most about 50 kN, at the most about 40 kN, at the most about 30 kN or at the most about 25 kN such as at the most about 20 kN.

In a specific embodiment, the invention provides a tablet comprising
i) a calcium-containing compound as an active substance,
ii) a vitamin D, and
iii) optionally one or more pharmaceutically acceptable excipients.

More specifically, the tablet may comprise
i) at least 200 mg of the calcium-containing compound (normal range 200-1500 mg),
ii) at least 5 µg of vitamin D (normal range 5-100 µg–1 µg=40 IU), and
iii) optionally one or more pharmaceutically acceptable excipients.

In a specific embodiment, the invention provides a tablet comprising
i) from about 50% to about 90% w/w of the calcium-containing compound,
ii) from about 0.00029% o about 0.0122 w/w of a vitamin D, and
iii) optionally one or more pharmaceutically acceptable excipients with the proviso that the total amount of ingredients corresponds to about 100% w/w.

In particular, the tablet may comprise
i) from about 50% to about 90% w/w of the calcium-containing compound,
ii) from about 5 to about 30% w/w of a sweetening agent,
iii) from about 0.12% to about 4.9% w/w of a vitamin D including a protective matrix, as delivered by supplier.
iv) optionally one or more pharmaceutically acceptable excipients with the proviso that the total amount of ingredients corresponds to about 100% w/w.

Preparation of a Tablet According to the Invention

The method according to the invention may also comprise compression of a granulate obtained as described herein optionally in admixture with one or more pharmaceutically acceptable excipients.

In general, tablets can be prepared by any suitable process known to a person skilled in the art. A person skilled in the art will know how to employ the different techniques optionally with guidance from Remington's The Science and Practice of Pharmacy (2003) Normally, the amount of the calcium-containing compound in a tablet corresponds to from about 100 to about 1000 mg Ca such as, e.g., from about 150 to about 800 mg, from about 200 to about 700 mg, from about 200 to about 600 mg or from about 200 to about 500 mg Ca.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties.

The calcium-containing compound is normally admixed with one or more pharmaceutically acceptable excipients before compression into tablets. Such excipients include those normally used in formulation of solid dosage forms such as, e.g. fillers, binders, disintegrants, lubricants, flavouring agents, colouring agents, including sweeteners, stabilizing agents, etc.

In the following are given examples of excipients suitable for use in a tablet prepared according to the present invention.

| Excipient | Concentration [% of formulation] |
| --- | --- |
| Sweetening agents | 5-30, if present |
| Artificial sweeteners | 0.05-0.3, if present |
| Flavours | 0.1-3, if present |
| Disintegrating agents | 0.5-5, if present |
| Glidant and lubricants | 0.1-5, if present |
| Fillers/diluents/binders | 0.1-40, if present |
| Film forming agents | 0.1-5, if present |
| Film additives | 0.05-5, if present |

Sweetening Agents

Examples of suitable sweeteners include dextrose, erythritol, fructose, glycerin, glucose, inositol, isomalt, lactitol, lactose, maltitol, maltose, mannitol, sorbitol, sucrose, tagatose, trehalose, xylitol, etc. Sorbitols e.g. Neosorb P100T, Sorbidex P166BO and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF, Gaio Tagatose and Manitol available from Palatinit, Arla Foods and Roquette, Freres respectively. Sorbitol has a sweetening effect (compared to sucrose) of 0.55; maltitol that has a sweetening effect of s1; xylitol that has a sweetening effect of 1, isomalt that has a sweetening effect of <0.5, etc. The sweetening effect may be of value in connection with choosing the individual sweetening agents. Thus, if a decreased tablet weight and volume are desired, it is suitable to choose a sweetening agent having a high sweetening effect.

Artificial Sweeteners

Acesulfam potassium, alitame, aspartame, cyclamic acid, cyclamate salt (e.g. calcium cyclamate, sodium cyclamate), neohesperidine dihydrochalcone, neohesperidine hydrochloride, saccharin, saccharin salt (e.g. ammonium saccharin, calcium saccharin, potassium saccharin, sodium saccharin), sucralose, taumatin and mixtures thereof.

Flavours

Aprocot, Lemon, Lemon/Lime, Lime, Orange, Mandarine, such as Aprocot 501.110 AP0551, Lemon 501.051 TP0551, Lemon 501.162 AP0551, Lemon/Lime 501.053 TP0551, Lime 501.054 TP0551, Orange 501.071 AP0551, Orange TP0551, Orange 501.434 $PO_{551}$, Mandarine 501.AP0551, Lemon Durarome 501.282 TDI1091 available from Firmenich, Kerpen, Germany or Juicy Lemon Flavouring T3602 available from TasteTech, Bristol, England or Lemon Lime Flavour Permseal 11029-31, Lemon Flavour Permaseal 12028-31, Lemon Flavour Ultradseal 96918-71 Available from Givaudan Schweiz AG, Kemptthal, Schweiz or Lemon Flavour Powder 605786, Lemon Flavour Powder 605897 available from Frey+Lau Gmbh, Henstedt-Ulzburg, Germany Sugar Alchols A sugar alcohol suitable for use in methods according to the invention is selected from the group consisting of isomalt, mannitol, sorbitol, xylitol, inositol, erythritol, lactitol, maltitol, and the like, and mixtures thereof. Normally, the concentration of the sugar alcohol, if present, in the composition comprising the calcium-containing compound is at the most about 40% w/w such as, e.g., from about 5% to about 40% w/w, from about 5% to about 35% w/w, from about 10% to about 30% w/w, from about 10% to about 30% w/w, from about 10% to about 25% w/w, cf. as discussed herein before.

Disintegrating Agents

Alginic acid-alginates, carboxymethylcellulose calcium, carboxymethylcellulose sodium, crospovidone, hydroxypropylcellulose, hydroxypropylmethylcellulose (HPMC), cellulose derivatives such as low-substituted hydroxypropylcellulose (e.g. LH 11, LH 20, LH 21, LH 22, LH 30, LH 31, LH 32 available from Shin-Etsu Chemical Co.) and microcrystalline cellulose, polacrilin potassium or sodium, polyacrylic acid, polycarbofil, polyethylene glycol, polyvinylacetate, polyvinylpyrrolidone (e.g. Polyvidon® CL, Poly-vidon® CL-M, Kollidon® CL, Polyplasdone® XL, Polyplasdone® XL-10); sodium car-boxymethyl starch (e.g. Primogel® and Explotab®), sodium croscarmellose (i.e. cross-linked car-boxymethylcellulose sodium salt; e.g. Ac-Di-Sol®), sodium starch glycolate, starches (e.g. potato starch, maize starch, rice starch), pre-gelatinised starch.

Those skilled in the art will appreciate that it is desirable for compressible tablets to disintegrate within 30 minutes, more desirable within 15 min, most desirable within 5 min; therefore, the disintegrant used preferably results in the disintegration of the tablet within 30 minutes, more preferable within 15 min, most preferable within 5 min. However, for tablets solely meant for chewing, a somewhat longer disintegration time is allowed.

Effervescent agent (e.g. mixture of sodium hydrogen carbonate (carbonates, alkaline, alkaline earth metals) and citric acid (tartaric acid, fumaric acid etc.)).

Glidants and Lubricants

Glidants and lubricants may be incorporated such as stearic acid, metallic stearates, talc, waxes and glycerides with high melting temperatures, hydrogenated vegetable oils, colloidal silica, sodium stearyl fumarate, polyethylenglycols and alkyl sulphates. Suitable lubricants include talc, magnesium stearate, calcium stearate, stearic acid, hydrogenated vegetable oils and the like. Preferably, magnesium stearate is used.

Fillers/Diluents/Binders

Dextrins, maltodextrins (e.g. Lodex® 5 and Lodex® 10), dextrose, fructose, glucose, inositol, erythritol, isomalt, lactitol, lactose (e.g., spray-dried lactose, α-lactose, β-lactose, Tabletose®, various grades of Pharmatose®, Microtose or Fast-Floc®), maltitol, maltose, mannitol, sorbitol, sucrose, tagatose, trehalose, xylitol, low-substituted hydroxypropylcellulose (e.g. LH 11, LH 20, LH 21, LH 22, LH 30, LH 31, LH 32 available from Shin-Etsu Chemical Co.), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), starches or modified starches (e.g. potato starch, maize starch, rice starch, pre-gelatinised starch), polyvinylpyrrolidone, polyvinylpyrrolidonehinyl acetate copolymer, agar (e.g. sodium alginate), calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, magnesium carbonate, magnesium chloride, methylcellulose, polyethylene glycol, polyethylene oxide, polysaccharides e.g. dextran, soy polysaccharide, sodium carbonate, sodium chloride, sodium phosphate.

Surfactants/Enhancers

Surfactants may be employed such as

Non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate)

cationic (e.g., benzalkonium chloride, benzethonium chloride and cetrimide).

Fatty acids, fatty alcohols and fatty esters, for example:

ethyl oleate, sodium oleate, lauric acid, methyl laurate, oleic acid, sodium caprate Dioctyl calcium sulfosuccinate, dioctyl potassium sulfosuccinate, dodecyltrimethylammonium bromide, hexadecyltrimethylammonium bromide, trimethyltetradecylammonium bromide, polyoxyethylene ethers (polyoxyethylene-9-lauryl ether), sodium dodecyl sulphate, sodium dioctyl sulfosuccinate, sodium laurate, sodium 5-methoxysalicylate, sodium salicylate;

bile salts, for example:

sodium deoxycholate, deoxycholic acid, sodium cholate, cholic acid, sodium glycocholate, sodium glycodeoxycholate, sodium taurocholate, sodium taurodeoxycholate;

cytoadhesives, for example:

lectins (e.g. *Lycopersicon Esculentum* Agglutinin, Wheat Germ Agglutinin, *Urtica Dioica* Agglutinin).

N-acylated amino acids (especially N-[8-(2-hydroxy-4-methoxy)benzoyl]amino caprylic acid (4-MOAC), 4-[4-(2-hydroxybenzoyl)amino]butyric acid, sodium N[8-(2-hydroxybenzoyl)amino]-caprylate);

phospholipids, for example:

hexadecylphosphocholine, dimyristoylphosphatidylglycerol, lysophosphatidylglycerol, phosphatidylinositol, 1,2-di(2,4-octadecadienoyl)sn-glycerol-3-phosphorylcholine and phosphatidylcholines (e.g. didecanoyl-L-phosphatidylcholine, dilauroylphosphatidylcholine, dipalmitoylphosphatidylcholine, distearoylphosphatidylcholine), lysophosphatidylcholine is of particular interest;

cyclodextrins, for example:

β-cyclodextrin, dimethyl-β-cyclodextrin, γ-cyclodextrin, hydroxypropyl β-cyclodextrin, methyl cyclodextrin; especially dimethyo-β-cyclodextrin is of particular interest;

fusidic acid derivatives, for example:

sodium taurodihydrofusidate, sodium glycodihydrofusidate, sodium phosphate-dihydrofusidate; especially sodium taurodihydrofusidate is of particulare interest;

others:

sodium salts of e.g. glycyrrhizic acid, capric acid, alkanes (e.g. azacycloalkanes), amines and amides (e.g. N-methylpyrrolidone, Azone), amino acids and modified amino acids compounds (e.g. acetyl-L-cysteine), polyols (e.g. propyleneglycol, hydrogels), sulfoxides (e.g. dimethylsulfoxide), terpenes (e.g. carvone), ammonium glycyrrizinate, hyluronic acid, isopropyl myristate, n-lauryl-beta-D-maltopyranoside, saponins, DL-octanonylcamitine chloride, palmitoyl-DL-carnitine chloride, DL-stearoylcamitine chloride, acylcamitines, ethylenediaminedihydro-chloride, phosphate-dihydrofusidate, sodium CAP); especially n-lauryl-beta-D-maltopyranoside is of particular interest, alpha 1000 peptide, peptide MW<1000 comprising at least 6 mol % of aspartatic- and glutamic Acid, decomposed royal jelly, prebiotica, butyrate, butyric acid, vitamin $D_2$, vitamin $D_3$, hydroxy-vitamin $D_3$, 1.25-dihydroxy-vitamin $D_3$, spirulina, proteoglycan, soyahydrolysate, lysin, lactic acid, di-fructose-anhydrid, vylitol Ca-(lactate), hydrolyzate of casein in particular a caseinoglycomacropeptide, negative ionization of $CaCO_3$, acetylsalicylic acid, vitamin K, creatin.

Film Forming Agents

The dosage form may be provided with a coating. Hydrofilic film formers such as hydroxypropylmethylcellulose (HPMC) (e.g. HPMC E5, HPMC E15), hydroxyethylcellulose, hydroxypropylcellulose, polydextrose and maltodextrin, Sepifilm™ and Sepifilm™ LP available from Seppic S.A., Pharmacoat® available from Shin-Etsu Chemical Co, Opadry® and Opagloss® available from Colorcon and Kolicoat® available from BASF AG.

Film Additives

Acetylated monoglyceride, acetyltributyl, acetyltributyl citrate, acetyltriethyl citrate, benzyl benzoate, calcium stearate, castor oil, cetanol, chlorebutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, wax.

Other Aspects of the Invention

The present invention also relates to granulates and solid dosage form obtained by the method of the invention. More specifically, the present invention provides a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and wherein the granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and wherein the calcium-containing granulate has been obtained by the method according to the present invention;

a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the granulate has been obtained by the method according to the present invention;
a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the granulate has been obtained by the method according to the present invention;
a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the granulate has been obtained by the method according to the present invention;
a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the granulate has been obtained by the method according to the present invention;
a granulate comprising a calcium-containing compound, notably calcium carbonate or calcium phosphate or a mixture thereof, in a concentration of at least 60% wow such as, e.g., at least 70% w/w, at least 75% w/w, or at least 80% w/w and a sugar alcohol in a concentration of about 25% w/w, and wherein the granulate has been obtained by the method according to the present invention;
a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the calcium-containing granulate has been obtained by the method according to the present invention;
a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the calcium-containing granulate has been obtained by the method according to the present invention;
a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the calcium-containing granulate has been obtained by the method according to the present invention;
a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the calcium-containing granulate has been obtained by the method according to the present invention;
a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% wow and a sugar alcohol in a concentration of about 25% w/w, and wherein the calcium-containing granulate has been obtained by the method according to the present invention;
a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the calcium-containing granulate has been obtained by the method according to the present invention;
a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the calcium-containing granulate has been obtained by the method according to the present invention;
a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the calcium-containing granulate has been obtained by the method according to the present invention;
a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the calcium-containing granulate has been obtained by the method according to the present invention;
a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of about 25% w/w, and wherein the calcium-containing granulate has been obtained by the method according to the present invention;
a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the calcium-containing granulate has been obtained by the method according to the present invention;
a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% wow such as, e.g., at least 70% w/w, at least 75% w/w, or at least 80% w/w and a sugar alcohol in a concentration of at least 15% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of about 25% w/w, and wherein the calcium-containing granulate has been obtained by the method according to the present invention.

Furthermore, the invention provides tablets, notably chewing tablets, comprising one or more of the above-mentioned granulates or compositions.

The invention is further illustrated in the following non-limiting examples
Materials and Methods
Methods
Crushing strength: According to Ph.Eur. 2.9.8
Tablet height Using a Micro 2000 (made by Moore & Wright (Sheffield) Ltd)
In the examples below, the following materials have been employed:

| Scoralite 1 B mainstream | Scora Watrigant S.A., France | Calcium carbonate |
| Xylitol CM 50 | Danisco Sweeteners, Kotka, Finland | Xylitol |
| Kollidon 30 | BASF AG, Ludwigshafen, Germany | Polyvinyl-pyrrolidone 30 (PVP 30) |
| Magnesium stearate | Peter Greven Netherland C.V | Magnesium stearate |
| Sorbidex P 166BO | Cerestar, Mechelen, Belgium | Sorbitol |
| Neosorb P100T | Roquette Freres, Estrem, France | Sorbitol |

The following non-limiting examples are designed to illustrate the invention. In order to provide guidance for a person skilled in the art of how to select process parameters as well as how to select suitable ingredients as well as suitable qualities thereof, the present examples are mainly focused on a relatively fixed composition of ingredients. However, a person skilled in the art will know how to adjust the process parameters as well as ingredients and qualities thereof based on the content herein. Accordingly, the present invention is not limited to the specific compositions mentioned in the examples below.

EXAMPLES

Example 1

Wet Granulation, Design of Experiment and Manufacture of Granulates

The purpose of the present examples was to investigate whether a process involving a fast and intensive addition of a granulation fluid to a calcium-containing composition combined with a short and intensive wet massing phase results in a granulate that has suitable properties with respect to compactability and compressibility and whether the tablets obtained are suitable for use in the treatment of conditions where calcium is indicated. As mentioned hereinbefore, the porosity of the calcium-containing tablets have been found to be an important parameter in judging whether the tablets e.g. are suitable as chewable tablets (especially with respect to an acceptable taste and mouth feel).

111.8 kg calcium carbonate (mean particle size approximately 5-25 μm) was mixed with 35.0 kg sorbitol in a Nautamixer and afterwards transferred to a hopper. For a few experiments, the below described experiment 6 and 7, calcium carbonate was used alone. Sorbitol was used in two different qualities, one with a mean particle size of approximately of 110 μm (coarse) and one with a mean particle size of approximately of 40 μm (fine).

The following binder solutions were manufactured:
1) 3 kg Povidone 30 (PVP 30) was dissolved in 27 kg purified water.
2) 9 kg PVP 30 was dissolved in 21 kg purified water.

Granulation was performed in a Schugi Flexomix FX-160 with a batch size of approximately 50 kg and a position of the knives of +2. The rotation speed of the mixer shaft was varied between 2500 rpm 4000 rpm. The feed of the calcium carbonate/sorbitol mixture was controlled by use of a K-tron T65 pre-feeder with agitator and a K-tron constant weight feeder WF300. The flow of powder mixture was maintained at 500 kg/h.

The binding solution was added by atomization, and the liquid flow was varied between 21 kg/h and 68 kg/h to obtain a wet granulate.

The wet granulate was transferred to a fluid bed dryer, inlet air temperature was varied between 50° C. and 110° C., and the granulate were dried to a product temperature of approximately 45° C. For processes without sorbitol the drying process was stopped at a product temperature of 55° C. The dried granulate was passed though a 1500 μm sieve.

Design of the Experiments

| Experiment | 1 | 2 | 3 | 4 | 5 | 6 | 7 |
|---|---|---|---|---|---|---|---|
| Comment | | | | | | | |
| Sorbitol coarse | + | + | + | + | + | − | − |
| pvp konc (%) | 10 | 10 | 10 | 30 | 0 | 30 | 30 |
| rpm | 3000 | 3000 | 3500 | 3500 | 3500 | 4000 | 4000 |
| Liquid flow rate kg/h | 39 | 30 | 21 | 28 | 22 | 68 | 41 |
| Liquid/powder ratio (%) | 7.2 | 5.7 | 4 | 5.3 | 4.2 | 12 | 7.6 |

| | | | | | | |
|---|---|---|---|---|---|---|
| Inlet temp. (° C.) | 50-80 | 60-80 | 80-100 | 80-90 | 80-90 | 110 | 110 |
| Bulkdens | 0.75 | 0.727 | 0.723 | 0.755 | 0.724 | 0.989 | 0.912 |
| End product temp. (° C.) | | | | 45 | 45 | 55 | 55 |

| Experiment | 8 | 9 | 10 | 11 | 12 | 13 |
|---|---|---|---|---|---|---|
| Comment | | | | | replic 11 | |
| Sorbitol coarse | + | + | | | | |
| Sorbitol fine | | | + | + | + | + |
| pvp konc (%) | 30 | 30 | 30 | 30 | 30 | – |
| rpm | 3500 | 2500 | 3500 | 3500 | 3500 | 3500 |
| Liquid flow rate kg/h | 28 | 28 | 21 | 28 | 28 | 19 |
| Liquid/powder ratio (%) | 5.3 | 5.3 | 4 | 5.3 | 5.3 | 3.7 |
| Inlet temp. (° C.) | 80-90 | 80-100 | 80-90 | 80-90 | 80-90 | 80-90 |
| Bulkdens | 0.793 | 0.729 | 0.734 | 0.726 | 0.734 | 0.612 |
| End product temp. (° C.) | 45 | 45 | 45 | 45 | 45 | 45 |

The liquid flow rate and the concentration of PVP 30 influence the total amount of PVP 30 added. This means that low liquid flow rate and low PVP 30 concentration result in low amount of PVP 30 in the granulate.

Reference granulates using high shear mixer- and fluid bed technologies were manufactured (experiment 14 and 15).

High Shear Mixer Granulate (Experiment 14)

A solution of 30 g polyvinylpyrrolidone 30 and 250 g purified water was manufactured. 4534.2 g calcium carbonate and 1414.8 g sorbitol were mixed in a Fielder PMA25 high shear mixer for 1 minute at 110 rpm (impeller speed) and 1500 rpm (chopper speed). The powder mixture was granulated by adding the polyvinylpyrrolidone 30 solution at a rate of 140 g/minute and a mixer speed of 110 rpm (impeller speed) and 1500 rpm (chopper speed), the solution was atomized. The moistened powder mass was wet massed for 2 minutes at a mixer speed of 110 rpm (impeller speed) and 1500 rpm (chopper speed). The wet granulate was dried on trays at 40° C. for 8 h. The dried granulate was passed through a sieve 1000.

Fluid Bed Granulate (Experiment 15)

The process was carried out as described in Example 1 of WO 00/28973 using the same amounts of ingredients as described above. The polyvinylpyrolidone solution was sprayed onto the fluidized bed (the fluidized mixture of calcium carbonate and sorbitol) at a rate of 40 g/min. Spraying was effected into air at an inlet temperature of 45° C. and at ambient pressure. Air at 70° C. was then passed through the sprayed granulate until it was dry.

The granulates were characterized by sieve analysis using the following sieves 1000 µm, 500 µm, 300 µm, 250 µm, 180 µm, 125 µm and 0 µm (below 125 µm).

The granulates were mixed with 0.75% w/w magnesium stearate by use of a Erweka tumbling mixer at 27 rpm for 5 minutes, batch size of approximately 6 kg. Tablets were manufactured by use of a Korsch PH106 instrumented rotary press and 16 mm round punches.

Target of tablet mass: 1600 mg

Target of compression force: 10 kN, 17 kN and 24 kN.

Die table rpm: 20

The tablets were characterized by crushing strength (maximal detectable strength is 200 N) and tablet height measured two days after manufacture.

In the following examples is given a discussion of the experiments.

Example 2

Impact of Process Parameters, Sorbitol Particle Size, Concentration of PVP 30 and The Obtained Particle Size Distribution (psd) on Tablet Height and Tablet Crushing Strength At fixed granulate composition, tablet weight, tablet diameter and compression force the porosity of a tablet is proportional with the height of the tablet, i.e. comparing tablets prepared employing different process parameters the lesser height the tablet has, the lower porosity.

In the formulation of tablets, the porosity of the tablets is important, especially with respect to the mechanical strength of the tablets. Moreover, e.g. chewable tablets must not be too "hard", i.e. they must be easy to chew and, accordingly, especially the porosity of chewable tablets is important. To this end it should be noted that the present inventors have found that the wettability of the tablet is of great importance in order to avoid the unpleasant taste and mouth-feel of the calcium-containing compound contained in the tablet. The more porous the tablet is the easier it is to wett. Accordingly, it is important to prepare a tablet that has certain porosity. However, at the same time the size of the tablet should be kept at a convenient size. Moreover, the tablets must be sufficiently robust to withstand normal handling of the tablets during preparation, packaging, distribution and storage.

Based on experiment 1-5, 8-13, and 14-15, a Principal Component Analysis (PCA) analysis has been performed by use of Unscrambler™ (version 7.8). The results are shown in FIGS. 1 and 2A as Bi-plot. This type of plot can be used to interpret sample properties. Variables far away from the centre have the most pronounced impact. Samples lying in a extreme position in the same direction as a given variable are markedly influenced by this variable. The direction of a variable can be illustrated by a line through the centre. However, samples lying directly opposite, when using the centre as a fix point, of a given variable are also markedly influenced but in a negative way. In order to facilitate interpretation of FIGS. 1, 2A, 2B, and 2C give a basic description of how to compare principle components in a bi-plot. The distance, here named t, between the response of a variable in the bi-plot and origo, describes the impact of the variable in question. The longer the distance is from origo the higher the impact. When comparing an independent variable 1 with a dependent variable 2, the response, the closer the angles $\theta_1$ of the unit vectors of the compared variables are the higher impact the independent variable has on the response. When the angle between two vectors is close to 90° the variables are independent. When the angle is close to 180° the variables are inversely proportional to each other.

In the PCA analysis the following variables have been used

Tablet height (named "tablet højde)

Particle size distribution (psd) in the form of amount of granulate on each of the used sieves Compression force Liquid flow rate (named væskeflow)

Tablet crushing strength (named brudstyrke dag)

Sortitol (coarse)

Sorbitol (fine)

The most important results from the PCA analysis are:

| Tablets meant for chewing | Tablets meant for swallowing |
|---|---|
| Sorbitol particle size: | Sorbitol particle size: |
| Coarse particles favour high tablets; | Fine particles favour |
| See FIG. 1 and 2 | tablets of low height; |
| | See FIG. 1 and 2 |
| Amount of granulate on sieve 180 μm, that is between 180 μm and 250 μm: High amount leads to high tablets See FIG. 1 and 2 | Amount of granulate on sieve 500 μm, that is between 500 μm and 1000 μm: |
| Amount of granulate on sieve 125 μm, that is between 125 μm and 180 μm: High amount leads to high tablets. See FIG. 1 and 2. | High amount leads to tablets of low height See FIG. 1 and 2 |

Tablet height is inversely related to crushing strength

The impact on tablets meant for chewing of the amount of granulate on the sieves 125 μm and 180 μm, that is between 125 μm and 250 μm, is well described by the sum of the amount on the two sieves divided by two. This corresponds to a fictive particle size interval from 150 μm ((180−125)/2+125) to 215 μm ((250−180)/2+180). In the present context, this interval is denoted sieve "150" μm.

The particle size distribution (psd) can be controlled by the following parameters:

Coarse sorbitol particle favours the amount of granulate in the interval 125 μm to 250 μm Fine sorbitol particle size favours the amount of granulate in the interval 500 μm to 1000 μm.

High liquid flow rate favours the amount of granulate in the interval between 250 μm to 300 μm and some larger granules; above 1000 μm Based on the analysis above it can be concluded that i) optimal conditions for manufacturing tablets meant for chewing is the use of coarse sorbitol particles and proper control of liquid flow rate equals to approximately 25-35 kg/h ii) the ideal granulate for high tablet heights and thereby easily chewable tablets has a psd that contains high proportions of a particle size between 150 μm and 215 μm.

iii) optimal conditions for manufacturing tablets meant for swallowing is the use of fine sorbitol particles and high amount of PVP 30 (see example 3).

Example 3

Comparing Tablet Height and Crushing Strength from Tablets Based on the Fluid Bed-, High Shear Mixer- and Schugiflex Technologies Tablet heights and crushing strengths from experiments 1-5, 8-13 and 14-15 are shown in FIGS. 3-6.

An analysis of the experiments using tablets based on fluid bed or high shear mixer granulation as reference shows that:

Reference Fluid bed:
Based on experiments 4, 8 and 9 it has been shown that tablets with height and crushing strength comparable to fluid bed based tablets are obtainable by proper control of the process parameters.
Experiment 1, 3 and 5 deviates from the reference. This can be explained by the lack of or the low level of binder (PVP 30).

Reference High shear mixer
Experiment 10, 11 and 12 has higher crushing strength and somewhat lower tablet heights
Experiment 2 and 13 has lower crushing strength and comparable tablet heights. The low crushing strength can be explained by the lack of or the low level of binder (PVP 30)

Comparing experiment 8 with experiment 11 illustrates the importance of the sorbitol particle size distribution. Tablets from experiment 8 have higher tablet height and lower tablet crushing strength than tablets from experiment 11. The experiments only differ with respect to sorbitol particle size.

Based on the analysis above it can be concluded that by use of a technology with a short and intensive wet massing phase granulates similar to what can be obtained from a fluid bed and a high shear mixer can be produced. Moreover, and more importantly granulates can be obtained that cannot be produced by a fluid bed or a high shear mixing process, namely granulates leading to tablets having porosities between that obtained using a fluid bed and a high-shear mixer process, respectively This means that tablets ideal for either chewing or swallowing can be manufactured using said technology.

Example 4

Impact of Addition of Extragranular Sorbitol (Fine) on Tablet Height and Crushing Strength The granulate from experiment 6 was admixed with either sorbitol (fine) or xylitol. The granulate from experiment 7 were admixed with sorbitol. The amounts of sorbitol and xylitol correspond to the amounts described in Example 1.

Figure 7:
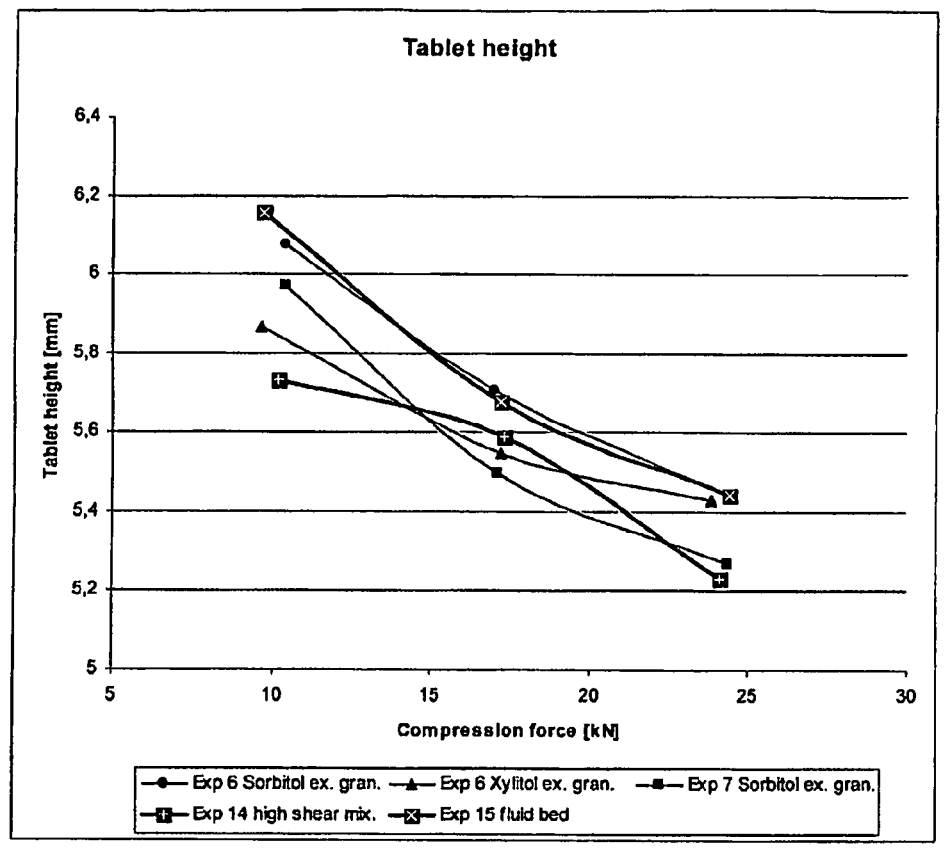
FIG. 7 illustrates the tablet height, impact of extra granular sorbitol and xylitol.
Figure 8:
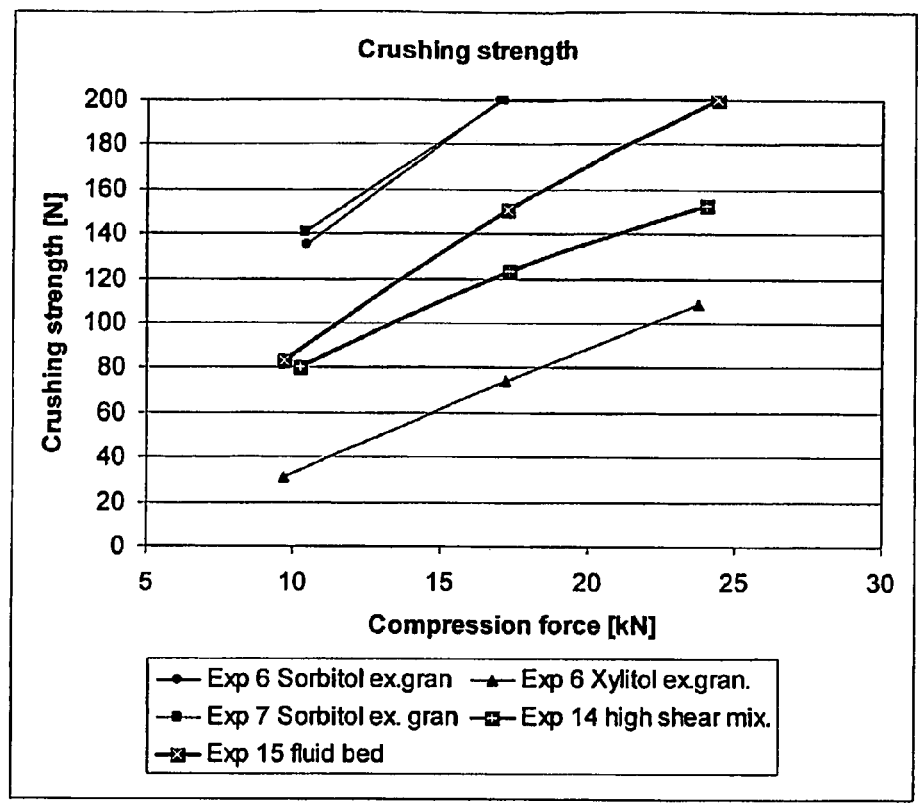
FIG. 8 illustrates the tablet crushing strength, impact of extra granular sorbitol and xylitol.

Tablet heights and crushing strengths from experiments 6 and 7 are shown in FIGS. 7-8.

An analysis based on FIGS. 7 and 8 shows that:
The addition of extragranular sorbitol significantly increases the crushing strength and results in the highest crushing strength of all experiments from 1-15
The addition of extragranular xylitol has a significantly lower impact on crushing strength than seen with sorbitol.
The addition of extragranular sorbitol or xylitol results in tablet heights in the range between what can be obtained from high shear mixer and fluid bed.
Crushing strengths comparable to tablets based on fluid bed and high shear mixer can be obtained by reducing the compression force and thereby achieving higher tablets indicating higher porosity. Probably even higher than what can be achieved by use of fluid bed.

Conclusion:

The use of extra granular sorbitol significantly increases the tablet crushing strength, which allows the compression force to be lowered. This will increase tablet height and thereby tablet porosity. This is especially useful for tablets meant for chewing.

The invention claimed is:

1. A method for the preparation of a granulate comprising calcium carbonate as an active substance, the method comprising,
   i) feeding a granulation chamber with a composition comprising the calcium carbonate, wherein the granulation chamber is fed with a feeding rate of from about 200 to about 1000 kg/h;
   ii) wet-massing the composition with a granulation liquid comprising a pharmaceutically acceptable binder for a time period of at the most 30 sec to obtain a wet granulate, wherein the granulation liquid is sprayed on the composition at a spray rate in a range of from about 15 to about 100 kg/h; and
   iii) drying the thus obtained wet granulate;
wherein a tablet prepared from the granulate has excellent taste and mouth-feel.

2. A method according to claim 1, wherein the wet-massing in step ii) is carried out in a time period of at the most about 1 sec.

3. A method according to claim 1, wherein the granulation chamber is fed with a feeding rate of from 300 to about 850 kg/h.

4. A method according to claim 1, wherein the granulation chamber is fed with a feeding rate of from about 1000 to about 1500 kg/h.

5. A method according to claim 1, wherein the granulation liquid is sprayed on the composition at a spray rate in a range of from about 15 to about 80 kg/h.

6. A method according to claim 1, wherein the granulation liquid is sprayed on the composition at a spray rate in a range of from about 75 to about 300 kg/h.

7. A method according to claim 6, wherein the granulation liquid is sprayed on the composition at a spray rate in a range of from about 50 to about 300 kg/h.

8. A method according to claim 1, wherein the feeding is continuously for a period of 1 day or more.

9. A method according to claim 1, wherein the composition comprising calcium carbonate is fed through the top of the granulation chamber and is passed through the chamber by means of gravity.

10. A method according to claim 1, wherein the pharmaceutically acceptable binder is selected from water-soluble binders.

11. A method according to claim 1, wherein the binder is selected from the group consisting of dextrins, maltodextrins, dextrose, fructose, glucose, inositol, erythritol, isomalt, lactitol, lactose, spray-dried lactose, $\alpha$-lactose, $\beta$-lactose, maltitol, maltose, mannitol, sorbitol, sucrose, tagatose, trehalose, xylitol, low-substituted hydroxypropylcellulose, microcrystalline cellulose, starches or modified starches, potato starch, maize starch, rice starch, pre-gelatinised starch, polyvinylpyrrolidone, polyvinylpyrrolidone/vinyl acetate copolymer, agar, sodium alginate, carboxyalkylcellulose, dextrates, gelatine, gummi arabicum, hydroxypropyl cellulose, hydroxypropylmethylcellulose, methylcellulose, polyethylene glycol, polyethylene oxide, polysaccharides, dextran and soy polysaccharide.

12. A method according to claim 1, wherein the granulation liquid is an aqueous medium.

13. A method according to claim 1 further comprising a step of mixing the granulate obtained with one or more pharmaceutically acceptable excipients.

14. A method according to claim 1 further comprising a step of adding one or more therapeutically, prophylactically and/or diagnostically active substance to the granulate obtained.

15. A method according to claim 14, wherein the active substance added is one or more nutrients.

16. A method according to claim 14, wherein the active substance is a D-vitamin.

17. A method for the preparation of a tablet, the method comprises compression of a granulate obtained as defined in claim 1 optionally in admixture with one or more pharmaceutically acceptable excipients.

18. A method according to claim 17, wherein the granulate is admixed with one or more further active substances.

19. A method according to claim 17, wherein the amount of calcium carbonate in a tablet corresponds to from about 100 to about 1000 mg Ca.

20. A method according to claim 1, performed by means of a Schugi Flexomix apparatus.

21. A method according to claim 1, wherein a binder is present in the calcium carbonate containing composition and/or the granulation liquid and in a concentration from about 0.1 to about 30% w/w.

22. A pharmaceutical composition comprising a granulate obtained as defined claim 1.

23. The pharmaceutical composition of claim 22 wherein the pharmaceutical composition is a dosage form.

24. The pharmaceutical composition of claim 23 wherein the dosage form is tablets, capsules or sachets.

25. The pharmaceutical composition of claim 22 wherein the pharmaceutical composition comprises at least 60% w/w of calcium carbonate.

26. The pharmaceutical composition of claim 22 wherein the pharmaceutical composition is in the form of a granulate.

27. The pharmaceutical composition of claim 22 wherein the pharmaceutical composition is in the form of a tablet.

28. The pharmaceutical composition of claim 22 wherein the pharmaceutical composition is in the form of a chewing tablet.

* * * * *